United States Patent [19]
Becker et al.

[11] Patent Number: 6,024,963
[45] Date of Patent: *Feb. 15, 2000

[54] POTENTIATION OF IMMUNOGENIC RESPONSE

[75] Inventors: Robert S. Becker, Henryville; Karen Biscardi, South Sterling; Laura Ferguson, Bethlehem; Lorne Erdile, Stroudsberg, all of Pa.

[73] Assignee: Connaught Laboratories, Inc., Swiftwater, Pa.

[*] Notice: This patent is subject to a terminal disclaimer.

[21] Appl. No.: 09/193,682

[22] Filed: Nov. 17, 1998

Related U.S. Application Data

[62] Division of application No. 08/470,278, Jun. 6, 1995, Pat. No. 5,837,264, which is a division of application No. 08/385,587, Feb. 8, 1995, Pat. No. 5,662,909, which is a continuation of application No. 07/943,173, Sep. 14, 1992, abandoned.

[51] Int. Cl.⁷ ........................ A61K 39/145; A61K 39/38; A61K 39/12
[52] U.S. Cl. .................... 424/206.1; 424/184.1; 424/204.1
[58] Field of Search ............................ 424/184.1, 187.1, 424/188.1, 204.1, 206.1, 207.1, 208.1

[56] References Cited

U.S. PATENT DOCUMENTS

| | | |
|---|---|---|
| 4,496,538 | 1/1985 | Gordon . |
| 4,619,828 | 10/1986 | Gordon . |
| 4,950,480 | 8/1990 | Barber et al. . |

FOREIGN PATENT DOCUMENTS

| | | |
|---|---|---|
| 0 366 238 | 2/1990 | European Pat. Off. . |
| WO 92/00055 | 1/1992 | WIPO . |

OTHER PUBLICATIONS

Balkovic et al., *Antiviral Research*, (1987), 8:151–160.
W.E. Paul, ed. *Fundamental Immunology*, (1984), p. 163 and tables 5–6.
W.R. Clark, ed., *Expermental Foundations of Modern Immunology*, (1980), p. 37.
Singer et al., *Ann. Rev. Immunol.*, (1983), 1:211–241.
Parker et al., *The FASEB Journal*, (Oct. 1991), vol. 5, pp. 2771–2784.
Eynon et al., Transplantation Proceedings, (Feb. 1991), vol. 23, No. 1, pp. 729–730.
Eynon et al., *J. Exp. Med.*, (Jan. 1992), vol. 175, pp. 131–138.
Myers, *The FASEB Journal*, (Aug. 1991), vol. 5, pp. 2547–2553.
Abbas et al., *J. Immun.*, (Sep. 1985), vol. 135, No. 3, pp. 1661–1667.
Grey et al., *J. Immun.*, (Dec. 1982), vol. 129, No. 6, pp. 2389–2395.
Malynn et al., *J. Immun.*, (Aug. 1985), vol. 135, No. 2, pp. 980–987.
Unanue, *Ann. Rev. Immunol.*, (1985), vol. 2, pp. 395–428.
Wireblauer et al., *Immun. Letters*, (1989/1990), vol. 23, pp. 257–262.
Katz et al., *Transplant. Rev.*, (1975), vol. 22, pp. 175–195.
Sprent, *J. Exp. Med.*, (1978), vol. 147, pp. 1142–1158.
Sprent, *J. Exp. Med.*, (1978), vol. 147, pp. 1159–1174.
Swierkosz et al., *J. Exp. Med.*, (1978), vol. 147, pp. 554–570.
Singer et al., *J. Exp. Med.*, (1981), vol. 154, pp. 501–516.
Lanzavecchia, *Nature*, (Apr. 1985), vol. 314, pp. 537–539.
Laver et al., *Virology*, (1976), vol. 69, pp. 511–522.
Butini et al., *J. Cell Biochem. Suppl.*, (1994) Abstract J30b, 18B.
Haynes, *Science*, (1993), vol. 260, pp. 1279–1286.
Maizels et al., *Eur. J. Immunol.*, (1980), vol. 10, pp. 509–515.
Becker et al., *Vaccines* 93, (1993), pp. 347–351.
Haynes, et al.: Update on the Issues of HIV . . . : DUODECIM: 28: pp. 39–41, 1996.
Haynes, et al.: Scientific and Social Issues of . . . : Science: vol. 260: pp. 1279–1286, May 1993.

*Primary Examiner*—Jeffrey Stucker
*Assistant Examiner*—Brett Nelson
*Attorney, Agent, or Firm*—Timothy R. Howe; G. Kenneth Smith; Connaught Laboratories Inc.

[57] ABSTRACT

An enhanced immune response to antigens, particularly normally weakly-immunogenic viral antigens, such as the HA antigen from influenza virus, is achieved by coadministering the antigen in two different physio-chemical forms, particularly to enable presentation of antigen both by B cells and accessory cells.

14 Claims, 9 Drawing Sheets

Dilution curves of an ELISA of sera from C3H mice immunized on days 0 and 21 with the indicated antigens. The mice were bleed on day 35.

FIG. 8

Secondary Immune Response to the Co-administration of OspA-L and OspA-NL

○ Pre-bleed serum
● 100ng OspA-L
▽ 500ng OspA-NL
▼ 100ng OspA-L + 500ng OspA-NL

FIG. 9

POTENTIATION OF IMMUNOGENIC RESPONSE

This is a division of U.S. application Ser. No. 08/470, 278, filed Jun. 6, 1995, U.S. Pat. No. 5,837,264, which is a division of U.S. application Ser. No. 08/385,587, filed Feb. 8, 1995, U.S. Pat. No. 5,662,909, which is a continuation of U.S. application Ser. No. 07/943,173, filed Sep. 14, 1992 now abandoned.

FIELD OF INVENTION

The present invention relates to vaccination and, in particular, to formulating vaccines so as to achieve an enhanced immunogenic response to an antigen.

BACKGROUND TO THE INVENTION

Vaccination is a procedure whereby an immune response to an antigen can be achieved to protect a host from infection. Some antigens elicit a strong immune response and some a weak response. Attempts have been made to enhance the immune response of weakly-immunogenic materials. The use of chemical adjuvants achieves such potentiation but generally such materials are toxic chemicals which cannot be used in humans.

Another procedure for achieving potentiation is to conjugate the weakly-immunogenic material to a strongly-immunogenic material and administer the conjugate in a vaccine. For example, a conjugate of the capsular polysaccharide of *Haemophilus influenzae* type b to diphtheria toxoid, as described in U.S. Pat. Nos. 4,496,538 and 4,619,828, or a conjugate of a weak antigen to a monoclonal antibody targeting antigen-presenting cells, as described in U.S. Pat. No. 4,950,480, may be employed.

SUMMARY OF INVENTION

In accordance with the present invention, there is provided a novel procedure of vaccination to elicit an enhanced antibody response to an antigen in a naive animal by administering the antigen in at least two different physio-chemical forms. The two different physio-chemical forms of the same antigen are administered simultaneously in a naive animal to achieve the greatest degree of potentiation and may be administered at a single or two injection sites.

In order for the enhanced immune response to be achieved, it is necessary that the animal to which the antigen is coadministered, including humans, be naive, i.e. the animal has not been previously been immunized by a highly-immunogenic form of the antigen. Co-administration of the antigen to a primed animal elicits no enhancement of immune response.

BRIEF DESCRIPTION OF DRAWINGS

FIGS. 1 and 2 contain graphical data of HAI titers achieved by various forms of HA antigen in naive guinea pigs, as detailed in Example 1 below;

FIGS. 3 and 4 and 5 contain graphical data of IgG anti-HA responses achieved by various forms of HA antigen in guinea pigs, as detailed in Example 2 below;

FIGS. 6 and 7 contain graphical data of HAI titers achieved by various forms of HA antigen in primed guinea pigs, as detailed in Example 3 below; and FIGS. 8 and 9 contain graphical data of the immune response achieved by various form of OspA in naive mice, as detailed in Example 4 below.

THEORY

While the applicant does not wish to be bound to any specific theory to explain why the present invention is effective in achieving potentiation of an antigenic response by the simultaneous administration of at least two different physio-chemical forms of the antigen, the following theoretical explanation can be made.

It is known that both B cells and accessory cells must present antigens to T-cells to initiate an antibody response to the antigen in naive animals (refs. 1, 2, 3, 4 and 5). B cells and accessory cells may have preferences for different physio-chemical forms of antigens. These references may result from B cells and accessory cells using different mechanisms for internalizing antigens.

B cells internalize antigens via specific binding to heir cell surface immunoglobulins (refs. 6, 7) and can present soluble antigens in concentrations as low as 1 ng/ml (ref. 8). Accessory cells, which are macrophages and dendritic cells, on the other hand, internalize antigens by non-specific phagocytizing and pinocytizing the antigens (ref. 9). Macrophages can present soluble antigens if they are at concentrations of approximately 100 $\mu$g/ml (ref. 8). other research (ref. 10) has demonstrated that the concentration of soluble antigen needed by macrophages can be decreased by binding the antigen to a particulate structure.

During the generation of an antibody response, B cells and accessory cells present antigens to T-cells at two different stages of T cell activation/differentiation. Research has demonstrated that naive T cells must first interact with antigen presenting accessory cells to become activated helper T cells (refs. 11, 12, 13, 14). The inventors believe that particulate forms of antigens, as employed herein, effectively mediate the accessory cell activation of naive T cells. This interaction, however, is insufficient to induce the B cells to respond to a T cell-dependent antigen. Direct cell-to-cell contact between B cells and activated helper T cells is required for the induction of antibody secretion from B cells (ref. 15). This interaction is mediated by B cells processing and presenting the antigen to activated T cell (ref. 16). This type of B cell-T cell interaction is termed cognate T cell help. The inventors believe that a soluble form of antigen employed herein best mediates B cells interacting with helper T cells.

The order of the two interactions is essential to bring about the required immune response in naive T cells. It has recently been shown that antigen presentation of B cells to naive T cells induces T cell tolerance rather than activation (refs. 2, 3). Since optimal immune responses require efficient antigen presentation by both B cell and accessory cells, such optimal response can be achieved in the present invention by simultaneously administering the antigen in two physio-chemical forms at either one or two sites of injection.

GENERAL DESCRIPTION OF INVENTION

As stated above, the novel method of achieving potentiated immune response in a naive animal, including humans, to an antigen is to administer the antigen simultaneously in at least two different physio-chemical forms. The invention is broadly applicable to a wide variety of antigens, particularly viral, bacterial, fungal, protozoan and parasite proteins, and is particularly useful with respect to antigens containing protective epitopes that normally exhibit a weak immunogenic response.

Among the viral antigens to which the invention may be applied are the gp120 and gp160 proteins of retroviruses especially HIV, the haemagglutinin antigen of influenza and other viral proteins associated with viral membranes.

The invention is illustrated hereinafter with respect to the haemagglutinin antigen (HA) from influenza virus but it will be apparent from the results given for the HA antigen and the discussion above that the invention has application to a wide range of antigens. Also presented below is data with respect to the immune response to the outer surface protein A (OspA) of the *B. burgdorferi* spirochete (i.e. a bacterial protein) in different physio-chemical forms. Lipidated OspA is a strong immunogen and hence coadministration with other forms of the OspA generally is not required. However, the results presented show the generality of the procedure.

One particular viral protein to which the invention may be applied is the gp120 protein of human immunodeficiency virus (HIV). The gp120 protein of HIV contains protective epitopes but is a poor immunogen. The immune response to gp120 can be potentiated by coadministering gp120 protein with inactivated HIV virions, gp160 or pseudovirions. The gp160 protein is the precursor protein that is proteolytically cleaved to form gp120 and gp40. The gp120 protein normally is associated with HIV virions via gp40. Purified gp120 protein is a soluble protein which is poorly immunogenic while viral particulate and gp160 protein are more immunogenic. Coadministration in accordance with the present invention may achieve an enhanced immune response to the gp120 protein.

The different physio-chemical form of the antigen for coadministration may vary widely, depending on the antigen chosen and the specific antigenic forms of the antigen which might be available. Preferably, the two forms are tailored to provide for antigen presentation both by B cells and by accessory cells to T-cells to initiate antibody response.

For example, one physio-chemical form may be soluble while the other may be insoluble and/or particulate, as in the case of HA antigen. Alternatively, the different physio-chemical form of the antigen may be a lipidated protein and a non-lipidated protein, as in the case of OspA antigen. In addition, the different physio-chemical forms of the antigen may comprise proteins with and without hydrophobic region. Further, the different physio-chemical forms of the antigen may comprise proteins which have been engineered, for example, by genetic engineering or chemical synthesis, to be provided with or without specific epitopes or regions.

EXAMPLES

Example 1

This Example demonstrates the effect of coadministration of different physio-chemical forms of the HA antigen from influenza virus.

Several different physio-chemical forms of HA exist, namely HA(p), split HA and inactivated whole virus. HA(p) is a highly purified form of HA that has had its hydrophobic tail removed and is soluble in water. Split HA is a detergent extracted and partially purified form of the HA antigen. Inactivated whole virus is formalin inactivated whole virus particles.

Split HA and inactivated whole virus are immunogenic in naive animals and humans. HA(p) is not immunogenic in naive animals or infants, even though it is antigenic in antibody-antigen reactions.

There was conducted two series of experiments in which guinea pigs were immunized with various physio-chemical forms of HA from the A/Taiwan influenza strain, alone or in combination, and their responses were measured by haemagglutination inhibition (HAI) titers, HAI titers being known to correlate well with protective immune responses. The results obtained in the experiments were plotted graphically and appear as FIGS. 1 and 2.

In these experiments, the amount of HA(p) was maintained constant (1.0 μg) and the amount of added whole inactivated virus was varied. Of the three amounts of whole inactivated virus employed (1.0 μg, 0.1 μg and 0.01 μg), immune responses were best potentiated by co-administration using 0.1 μg whole inactivated virus, as may be seen from FIGS. 1 and 2.

Figure 1:
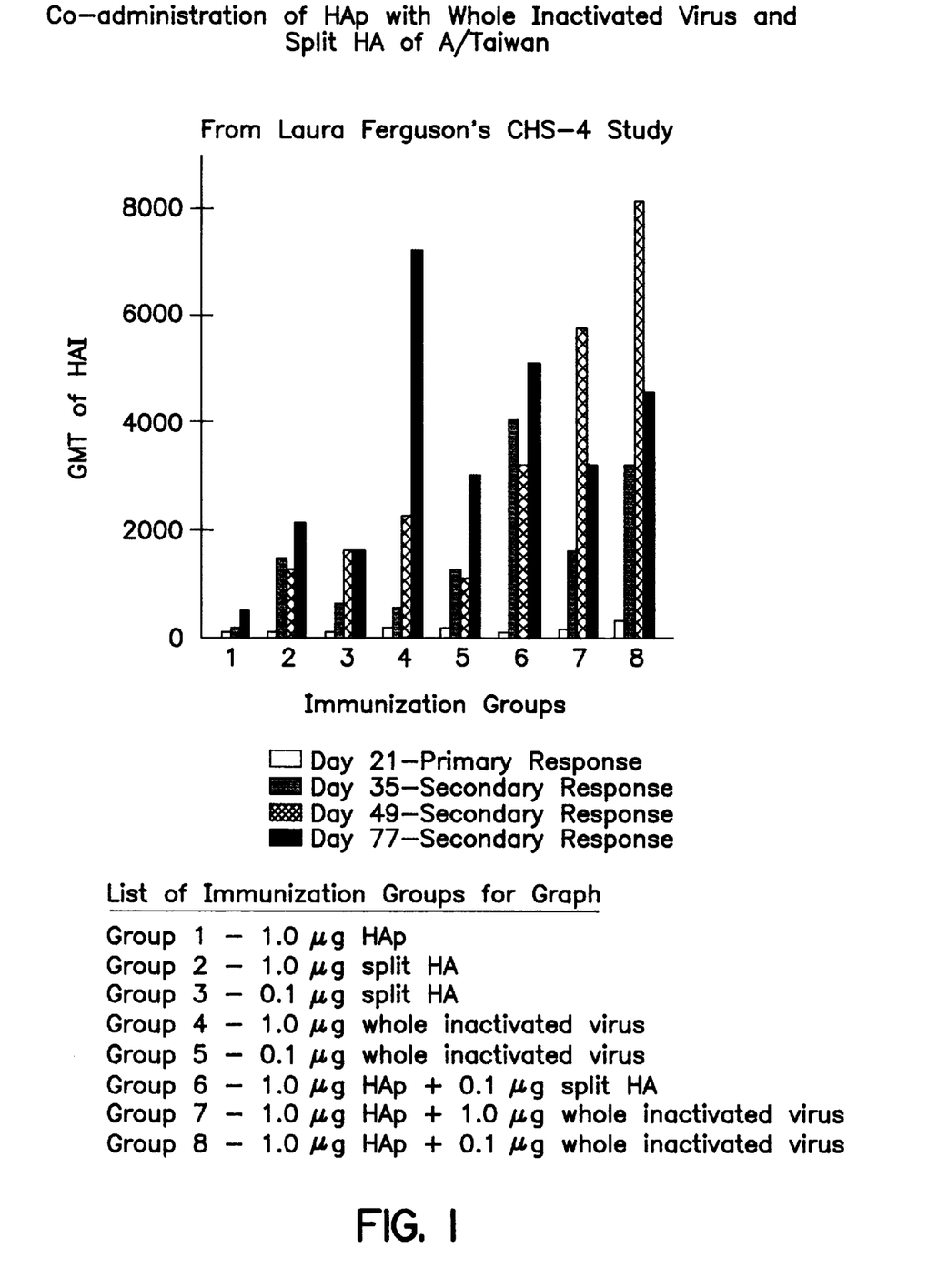
Figure 2:
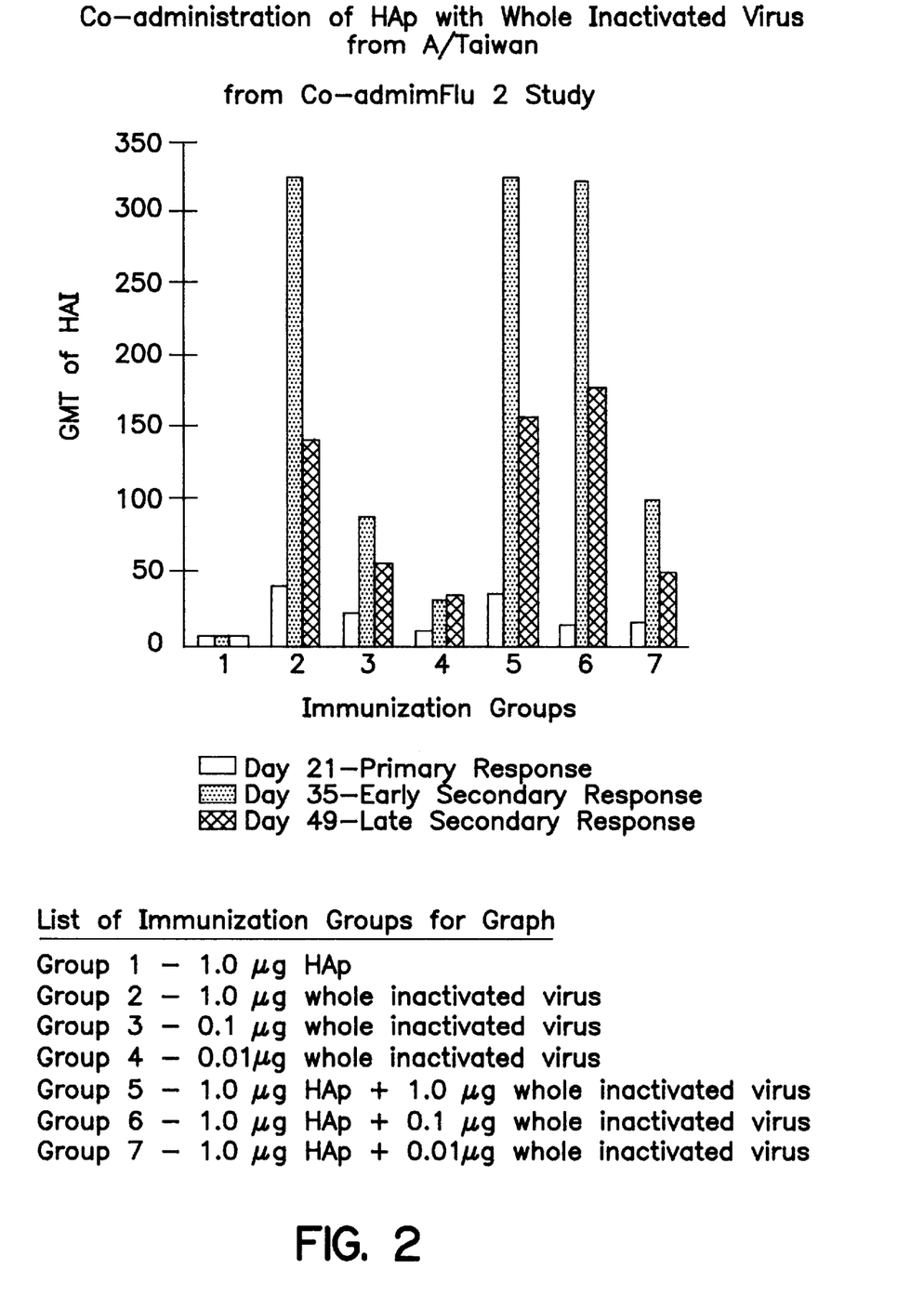

When the titers for this combination were compared to the titers for HA(p) or 0.1 μg whole inactivated virus alone, coadministration potentiated immune responses four to seven fold at two to four weeks after the boost. At the higher dose of 1.0 μg of whole inactivated virus, immune responses to coadministration were equal to the responses to the virus alone, again as seen in FIGS. 1 and 2. At the low dose of 0.01 μg whole inactivated virus, the immune response to both coadministration and whole inactivated virus alone were low (see FIG. 2). Since HAI titers correlate well with protective immune responses, these results suggest that coadministration enhances protective immune responses in guinea pigs.

The co-administration of split HA and HA(p) also enhanced anti-HA antibody responses in guinea pigs.

Figure 4:
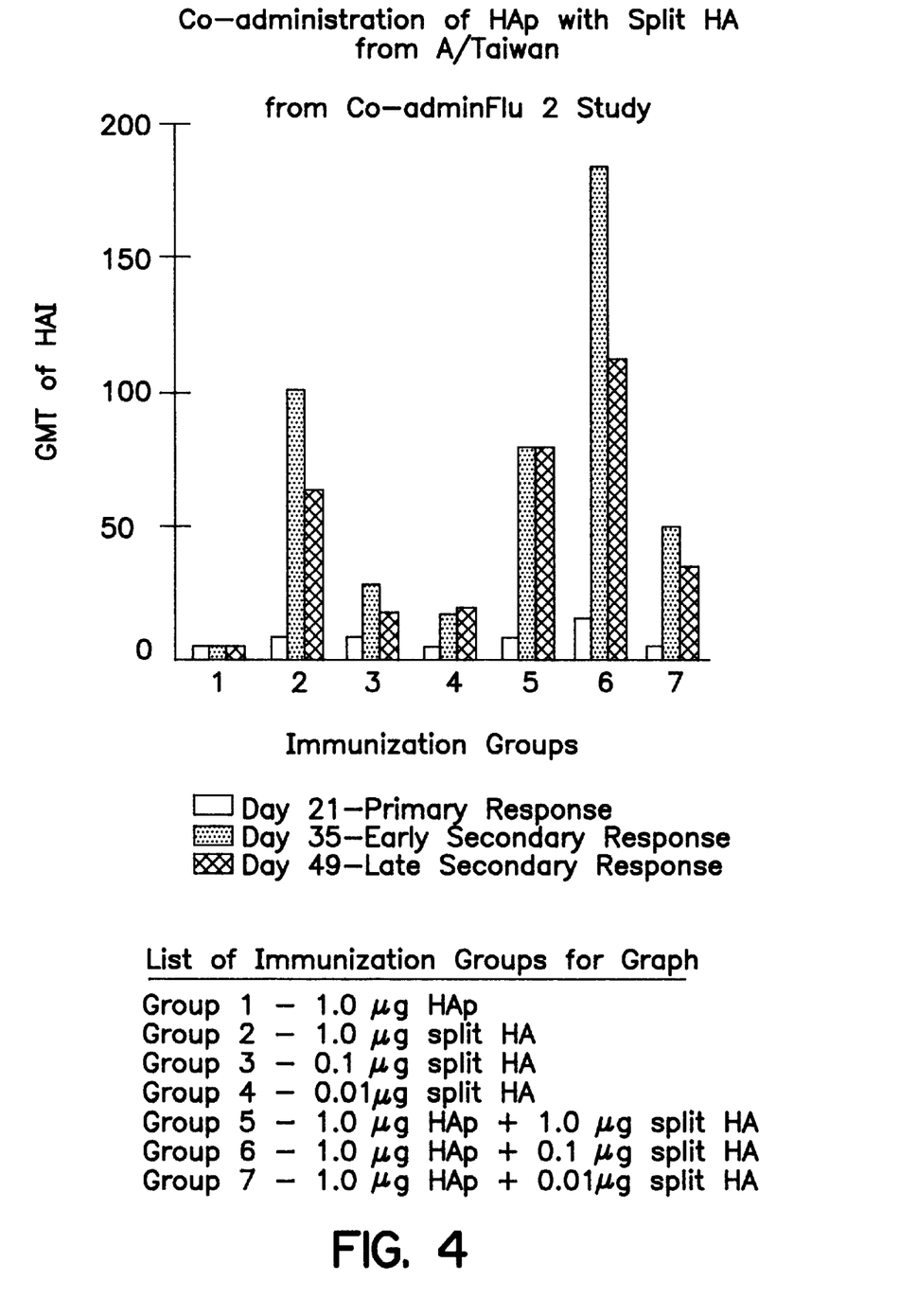

Maximal enhancement by coadministration was observed using 0.1 μg of HA(p) and 0.1 μg of split HA, as may be seen from the results of FIGS. 1 and 4. A three- to seven-fold enhancement in HAI titers was observed using these amounts of antigen.

Example 2

In addition to the results obtained in Example 1, antibody responses were analyzed by EIA (ELIZA immuno-assay) to determine whether the enhancement of HAI titers by coadministration was related to the total amount of IgG anti-HA antibody generated. In these experiments, HA-e (a highly-purified form of HA that retains its hydrophobic tail) was used to coat the wells of the EIA plate and anti-guinea pig IgG was used as a detecting antibody. The dilution curves of experimental antisera were compared to the dilution curve of a standard guinea pig anti-serum and, on the basis of that comparison, the units of IgG anti-HA were calculated in each sera.

Figure 3:
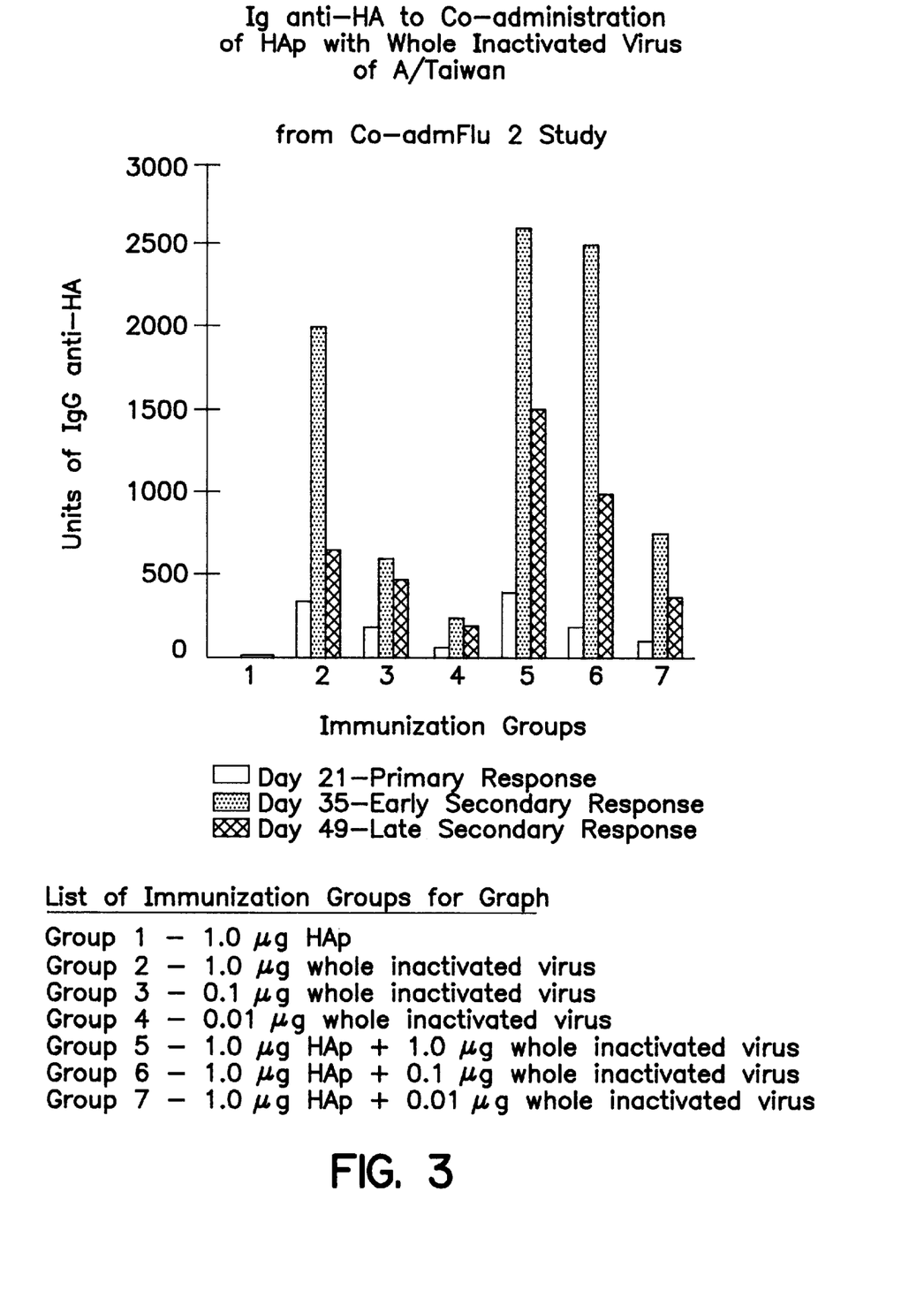

Using the same guinea pig sera, a good correlation was found when the results of the EIA, as seen in FIG. 3, were compared with the results of the HAI, as seen in FIG. 2. These results show that co-administration of the HA in different forms enhances the total amount of IgG generated against HA.

Figure 5:
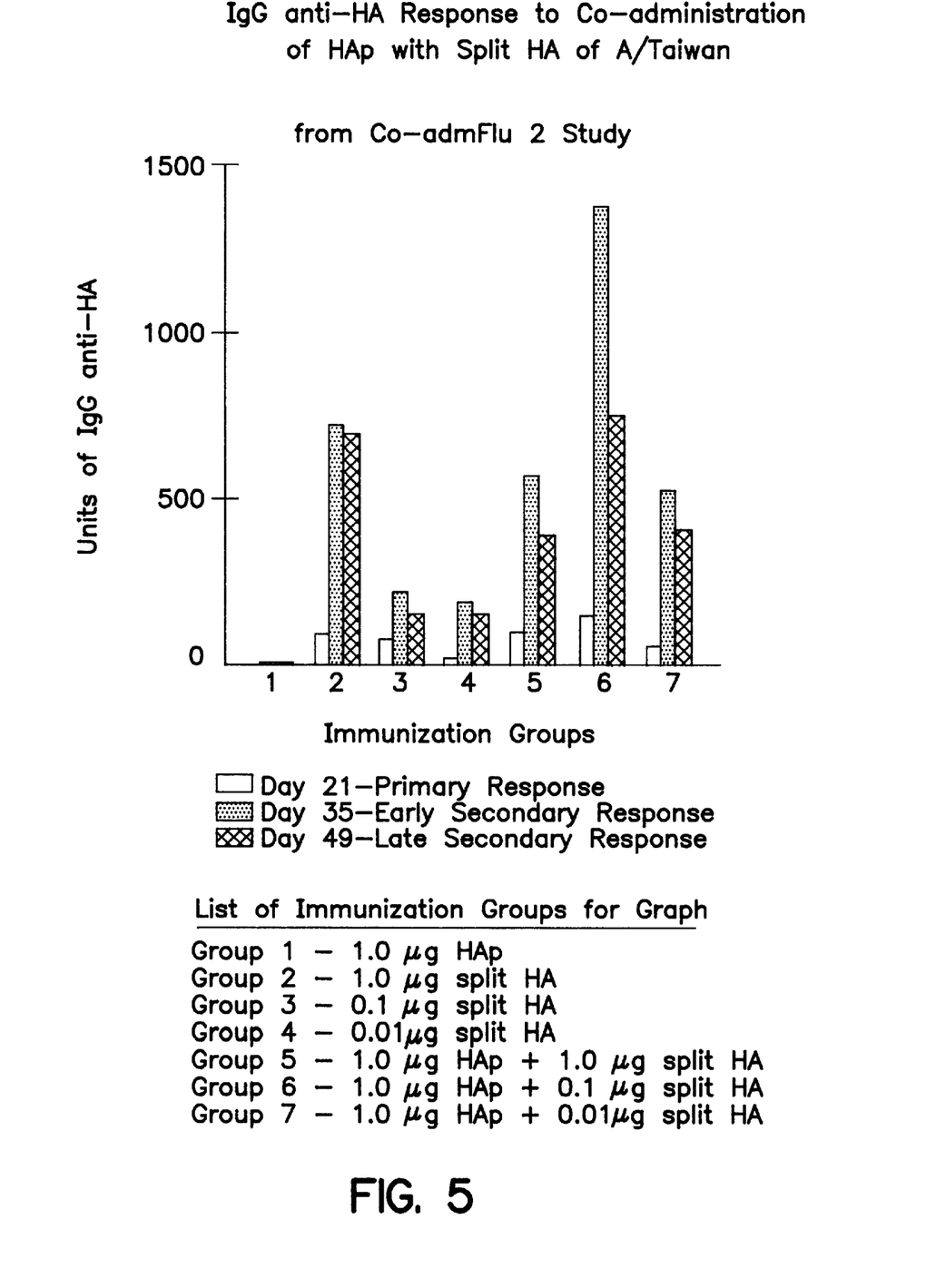

The results of EIA on sera from an experiment using split HA, as seen in FIG. 5, indicated that the increased HAI titers from co-administration were the result of increased amounts of anti-HA antibodies. From the results set forth in Examples 1 and 2, it is apparent that the levels of antibody generated to coadministration with split HA generally were less than those to coadministration with whole inactivated virus, as may be seen from FIG. 1 and a comparison of FIGS. 2 and 4 and FIGS. 3 and 5.

In the experiments reported in Examples 1 and 2, naive animals were used to evaluate coadministration.

Example 3

This example illustrates the effect of coadministration of HA in primed animals.

Figure 6:
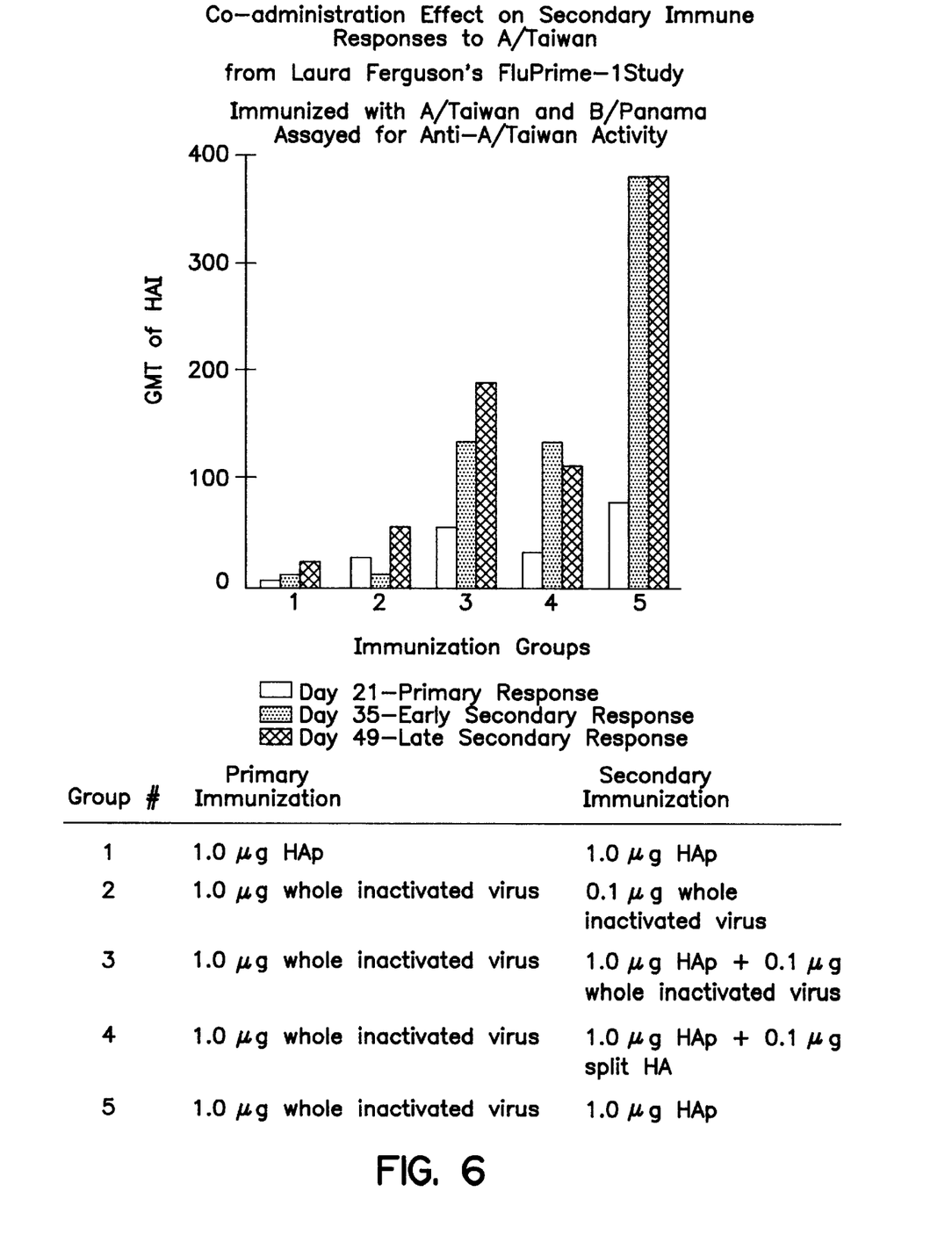
Figure 7:
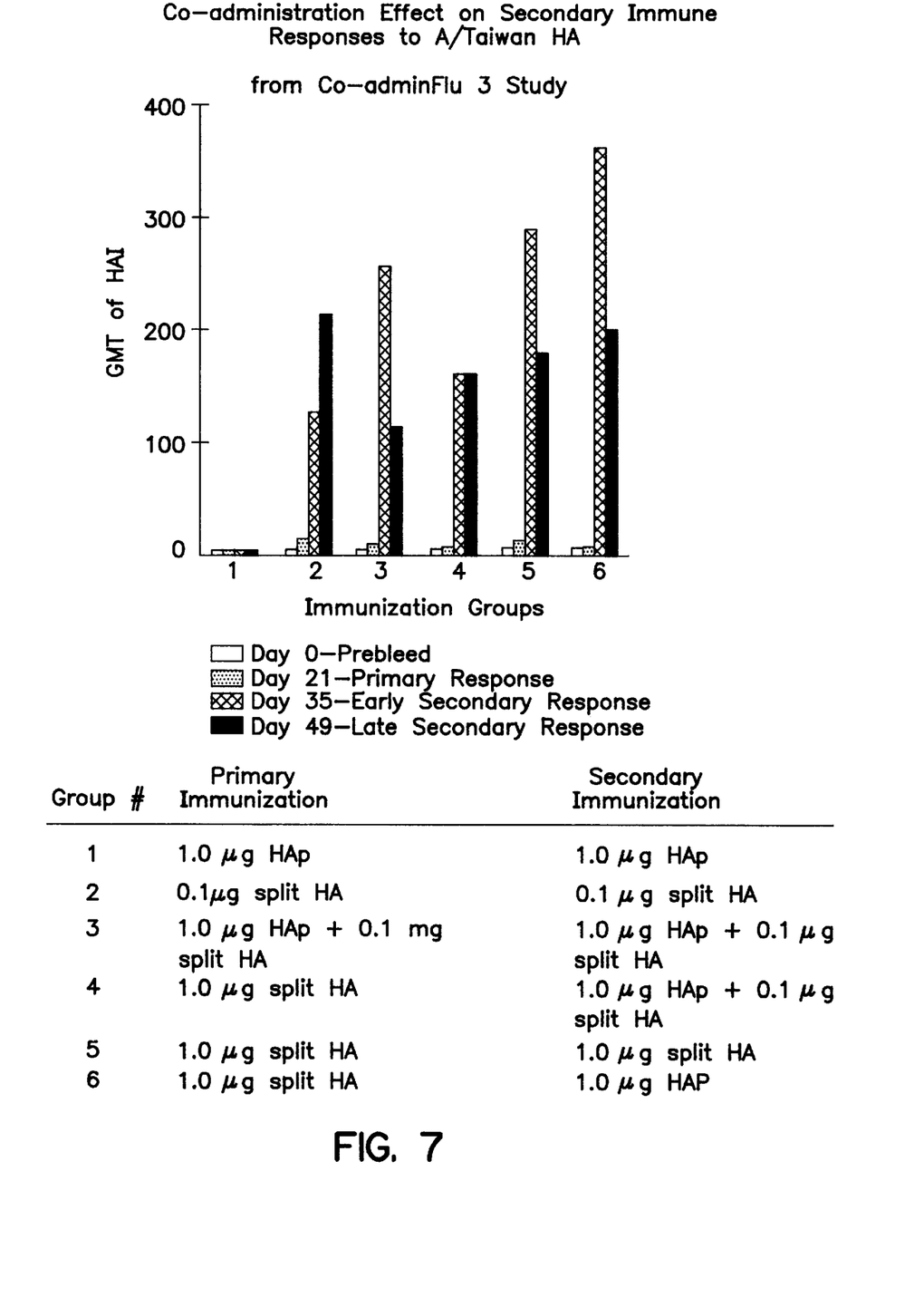

Guinea pigs were primed with either 1.0 μg of whole inactivated virus (results depicted in FIG. 6) or 1.0 μg of split HA (results depicted in FIG. 7). Three weeks later, the guinea pigs were given secondary immunization of either single flu antigen or coadministered flu antigens. The results shown in FIGS. 6 and 7 indicate that co-administration does not enhance anti-HA results in primed animals and hence the co-administration technique is useful only in naive animals, if an enhanced immune response is to be achieved.

These results also show that the superior antigen for recalling memory responses was HA(p) alone, while immunization with HA(p) at the primary and secondary immunization did not generate a significant immune response. These results show that HA(p) can recall memory immune responses to the HA antigen but cannot itself generate memory.

Example 4

This Example demonstrates the effect of different physio-chemical forms of the OspA protein of *B. buradorferi* spirochete.

OspA lipoprotein (OspA-L) is a very potent immunogen. Removal of the lipid moiety from OspA dramatically decreases its immunogenicity but not its antigenicity, as described in copending U.S. patent application Ser. No. 888,765 filed May 27, 1992, assigned to the assignee hereof and the disclosure of which is incorporated herein by reference.

Figure 8:
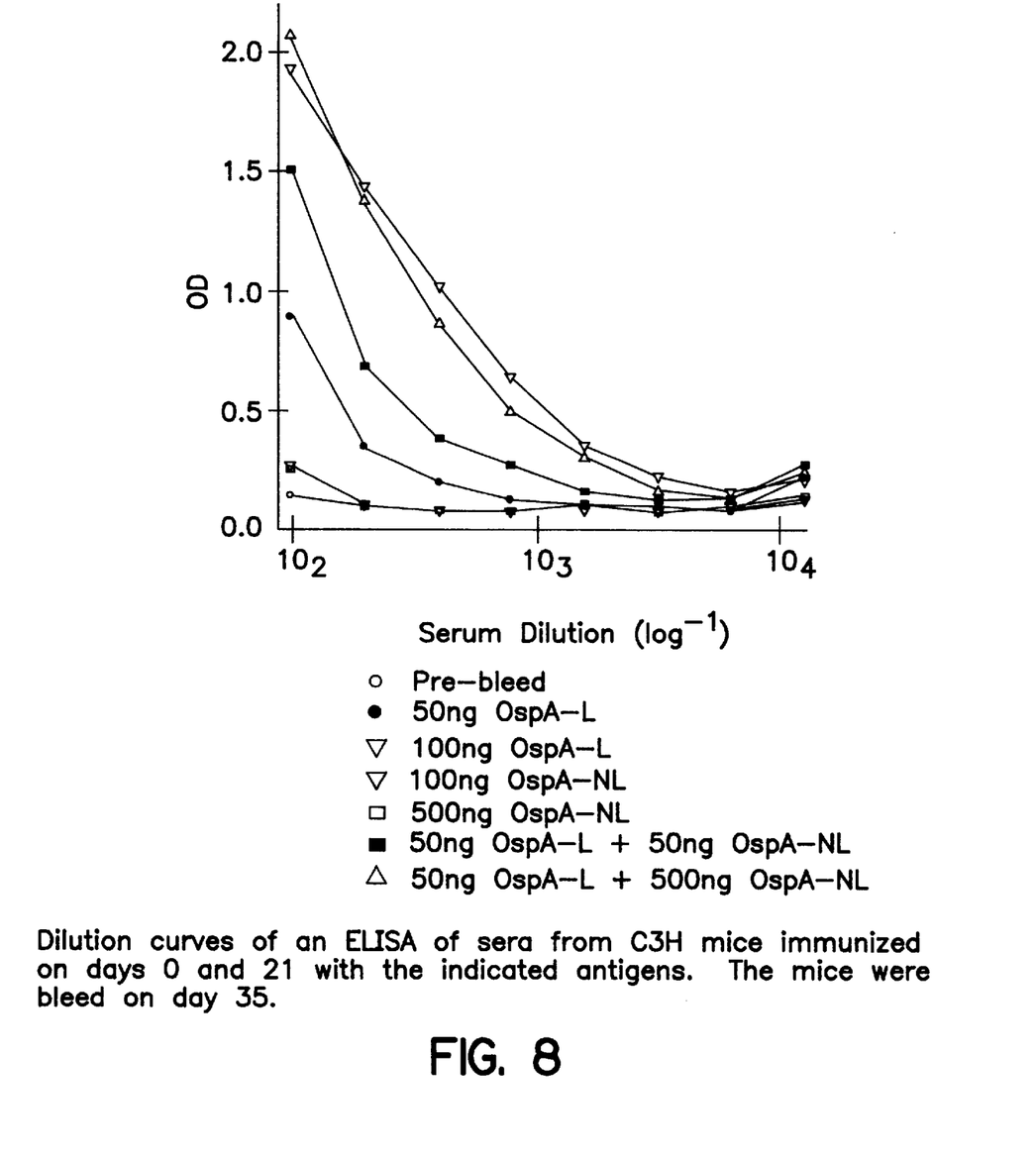
Figure 9:
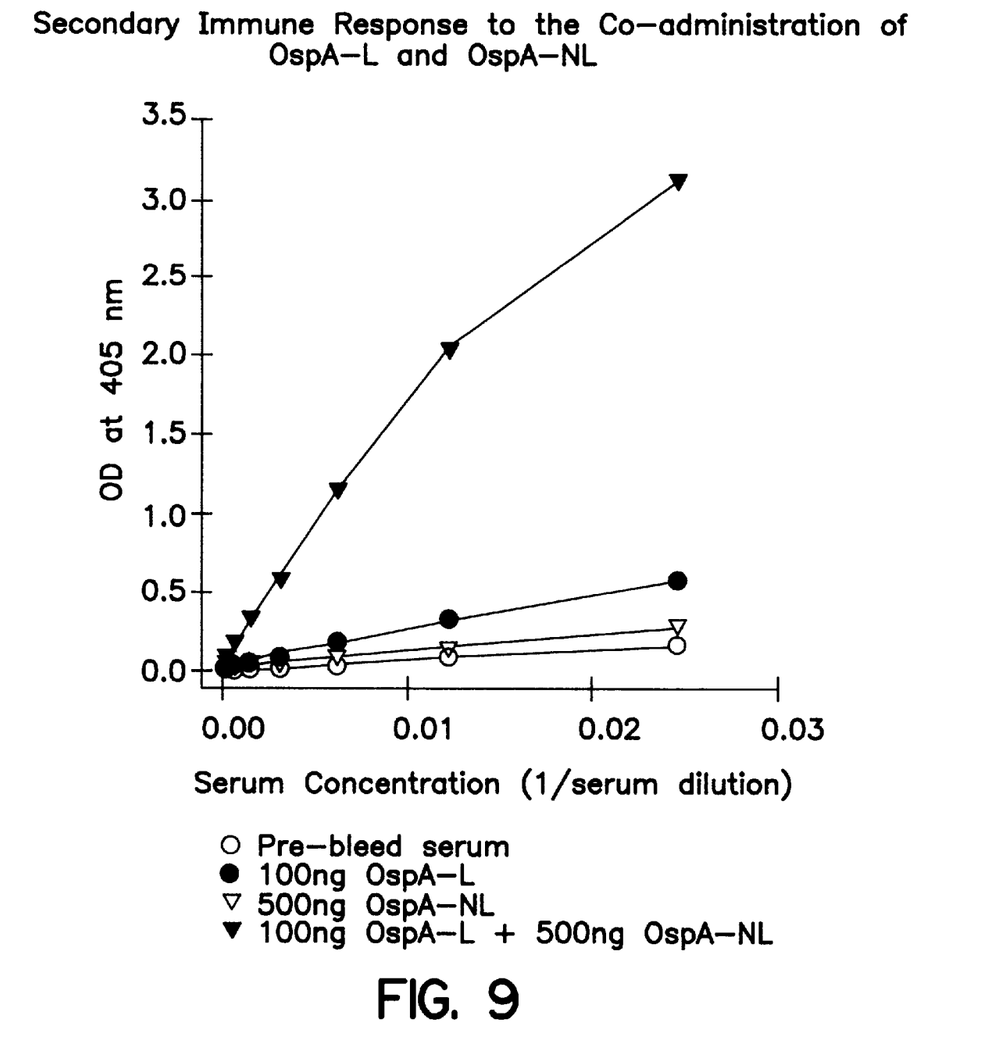

A small dose of OspA-L was coadministered to C3H/He mice with a large dose of OspA-NL and the response compared to the responses of OspA-L or OspA-NL alone. The mice were immunized at days 0 and 21 with the antigens and the mice were bled on day 35. The dilution curves of an ELISA assay of sera from the mice were plotted graphically and the results are shown in FIG. 8. Immune responses also are shown in FIG. 9.

As may be seen from this data, a potentiation of OspA response was achieved by coadministration of OspA-L and Ospa-NL relative to administration of OspA-L or OspA-NL alone.

SUMMARY OF DISCLOSURE

In summary of this disclosure, the present invention provides a novel method of obtaining an enhanced immune response to a viral antigen by coadministering the antigen in different physio-chemical forms. Modifications are possible within the scope of this invention.

REFERENCES

1. "Mechanisms of T cell-B cell Interaction", Singer et al. Ann. Rev. Immunol. 1983, 1:211–41.
2. "Antigen Presentation in Acquired Immunological Tolerance", Parker et al, The FASEB Journal, Vol. 5, Oct. 1991, pp. 2771–2784.
3. "Do Small B Cells Induce Tolerance", Eynon et al, Transplantation Proceedings, Vol. 23, No 1 (February) 1991: pp. 729–730.
4. "Small B Cells as Antigen-Presenting Cells in the Induction of Tolerance to Soluble Protein Antigens" by Eynon et al, J. Exp. Med. Vol. 175, January 1992, pp. 131–138.
5. "Role of B Cell Antigen Processing and Presentation in the Humoral Immune Response", Myers, The FASEB Journal, Vol. 5, August 1991, pp. 2547–2553.
6. "Antigen Presentation by Hapten-Specific B Lymphocytes", Abbas et al, J. Immun. Vol. 135, No. 3, September 1985, pp. 1661–1667.
7. "Requirements for the Processing of Antigen by Antigen-Presenting B Cells", Grey et al, J. Immun., Vol. 129, No. 6, December 1982, pp. 2389–2395.
8. "Antigen-Specific B Cells Efficiently Present Low Doses of Antigen for Induction of T Cell Proliferation", Malynn et al, J. Immun. Vol. 135, No. 2, August 1985, pp. 980–987.
9. "Antigen-Presenting Function of the Macrophage", Unanue, Ann. Rev. Immunol., 1985, 2: 395–428.
10. "Analysis of TX Lymphocyte Reactivity to Complex Antigen Mixtures by the Use of Proteins coupled to Latex Beads", Wirbelauer et al, Immun. Letters, 23 (1989/1990), 257–262.
11. "The Function and Interrelationships of T. Cell Receptors, Ir Genes and other Histocompatibility Gene Products", Katz et al, Transplant. Rev. (1975), Vol. 22, pp. 175–195.
12. "Restricted Helper function of F. Hybrid T Cells Positively Selected to Heterologous Erythrocytes in Irradiated Parental Strain Mice. I", Sprent, J. Exp. Med., 1978, Vol. 147, pp. 1142–1158.
13. "Restricted Helper function of F. Hybrid T Cells Positively Selected to Heterologous Erythrocytes in Irradiated Parental Strain Mice. II", Sprent, J. Exp. Med., 1978, Vol. 147, pp. 1159–1174.
14. "The Role of H-2-Linked Genes in Helper T-Cell Function", Swierkosz et al, J. Exp. Med., 1978, Vol. 147, pp. 554–570.
15. "Role of the Major Histocompatibility Complex in T Cell Activation of B Cell Subpopulations", Singer et al, J. Exp. Med., 1981, Vol. 154, pp. 501–516.
16. "Antigen-specific Interaction between T and B Cells", Lanzavecchia, Nature, Vol. 314, April 1985, pp. 537–539.

What we claim is:

1. A method for achieving an enhanced immune response to an antigen in a naïve animal, wherein a naïve animal is an animal which has not been previously immunized by a highly immunogenic form of the antigen, the method comprising simultaneously administering a viral protein antigen to the naïve animal in at least two different physio-chemical forms to provide a synergistic immune response to the antigen in the naïve animal greater than the immune response to the individual physiochemical forms of the antigen in the naïve animal wherein the antigen is HA from influenza virus.

2. The method of claim 1 wherein one of the physico-chemical forms favors presentation of the antigen by B cells to T cells in the naïve animal and the other of the physico-chemical forms favors presentation of the antigen by accessory cells to T cells in the naïve animal.

3. The method of claim 2 wherein one physicochemical form of the antigen is soluble while the other is insoluble and/or particulate.

4. The method of claim 3 wherein the soluble physicochemical form of the antigen is HA(p) and the other physicochemical form of the antigen is split HA or inactivated whole virus.

5. The method of claim 2 wherein one physicochemical form of the antigen is lipidated and the other physicochemical form is non-lipidated.

6. The method of claim 2 wherein one physicochemical form of the antigen is a protein having a hydrophobic region and the other physicochemical form is the protein lacking the hydrophobic region.

7. The method of claim 2, wherein one physicochemical form of the antigen is a protein engineered to contain a specific epitope and/or region and the other is the protein lacking such specific epitope and/or region.

8. The method of claim 1, wherein the animal is a human.

9. A vaccine for eliciting an immune response to an antigen in a naïve animal, wherein a naïve animal is an animal which has not been previously immunized by a highly-immunogenic form of the antigen, which vaccine comprises:
   a) a first physicochemical form of the antigen favoring presentation of the antigen by B cells to T cells in the animal,
   b) a second physicochemical form of the antigen favoring presentation of the antigen by accessory cells to T cells in the animal, and
   c) a physiologically-acceptable carrier for the first and second physiochemical forms of the antigen,
      whereby a synergistic enhanced immune response to the antigen is achieved upon administration of the vaccine to the naïve animal in comparison to either of the physicochemical forms administered alone, and wherein the antigen is a viral protein,
   wherein the antigen is HA from influenza virus.

10. The vaccine of claim 7 wherein the first physicochemical form of the antigen is soluble while the other is insoluble and/or particulate.

11. The vaccine of claim 10 the first physicochemical form of the antigen is HA(p) and the other is split HA or inactivated whole virus.

12. The vaccine of claim 7 wherein one physicochemical form of the antigen is lipidated and the other physicochemical form is not lipidated.

13. The vaccine of claim 9 wherein one physicochemical form of the antigen is a protein having a hydrophobic region and the other is the protein lacking the hydrophobic region.

14. The vaccine of claim 9 wherein one physicochemical form of the antigen is a protein engineered to contain a specific epitope and/or region and the other is the protein lacking such specific epitopes and/or region.

* * * * *